United States Patent [19]

Mader et al.

[11] Patent Number: 5,312,441
[45] Date of Patent: May 17, 1994

[54] METHOD AND APPARATUS FOR DISCRIMINATION OF VENTRICULAR TACHYCARDIA FROM SUPRAVENTRICULAR TACHYCARDIA AND FOR TREATMENT THEREOF

[75] Inventors: Steven J. Mader; John R. Lisowski, both of Minneapolis; Walter H. Olson, North Oaks, all of Minn.; Kenneth P. Huberty, Lutz, Fla.

[73] Assignee: Medtronic, Inc., Minneapolis, Minn.

[21] Appl. No.: 867,931

[22] Filed: Apr. 13, 1992

[51] Int. Cl.⁵ .............................................. A61N 1/36
[52] U.S. Cl. ....................................................... 607/5
[58] Field of Search ............ 128/419 D, 419 PG, 703, 128/705, 708; 607/5, 9, 14

[56] References Cited

U.S. PATENT DOCUMENTS

| | | | |
|---|---|---|---|
| 3,460,527 | 8/1969 | Karsh | 128/703 |
| 3,524,442 | 8/1970 | Horth | 128/703 |
| 3,552,386 | 1/1971 | Horth | 128/703 |
| 3,606,882 | 4/1972 | Abe et al. | 128/703 |
| 3,658,055 | 4/1972 | Abe et al. | 128/703 |
| 4,000,461 | 12/1976 | Barber et al. | 128/708 |
| 4,181,135 | 1/1980 | Andresen et al. | 128/703 |
| 4,375,817 | 3/1983 | Engle et al. | 128/419 D |
| 4,384,584 | 5/1983 | Zipes | 128/419 D |
| 4,523,595 | 6/1985 | Zibell | 128/419 D |
| 4,548,209 | 10/1985 | Wielders et al. | 128/419 D |
| 4,577,633 | 3/1986 | Berkovits et al. | 128/419 PG |
| 4,587,970 | 5/1986 | Holley et al. | 128/419 PG |
| 4,726,380 | 2/1988 | Vollmann et al. | 128/419 PG |
| 4,800,883 | 1/1989 | Winstrom | 128/419 D |
| 4,830,006 | 5/1989 | Haluska et al. | 128/419 D |
| 4,880,004 | 11/1989 | Baker, Jr. et al. | 128/419 PG |
| 4,880,005 | 11/1989 | Pless et al. | 128/419 PG |
| 4,949,719 | 8/1990 | Pless et al. | 128/419 D |
| 4,953,551 | 9/1990 | Mehra et al. | 128/419 D |
| 5,086,772 | 2/1992 | Larnard et al. | 128/419 D |

OTHER PUBLICATIONS

Experimental Ventricular Defibrillation with an Automatic and Completely Implanted System by Shuder et al., Transactions American Society for Artificial Internal Organs 16:207, 1970.
Automatic Implantable Cardioverter–Defibrillator Structural Characteristics by Mower et al in PACE, vol. 7, Nov.-Dec., 1984, Part II, pp. 1331-1334.
Automatic Tachycardia Recognition by R. Arzbaecher et al., PACE, May-Jun., 1984 pp. 541-547.
Reliable R-Wave Detection from Ambulatory Subjects by Thakor et al., published in Biomedical Science Instrumentation vol. 4, pp. 67-72, 1978.

*Primary Examiner*—Lee S. Cohen
*Assistant Examiner*—Jeffrey R. Jastrzab
*Attorney, Agent, or Firm*—Reed A. Duthler; Harold R. Patton

[57] ABSTRACT

An implantable cardioverter including apparatus for measuring the width of a patient's R-wave in order to determine whether or not to deliver an antitachycardia therapy. The means for measuring the width of the R-wave comprises a digitizing means for converting electrical signals from the ventricle to digital signals and means for analyzing the digitized signals to determine the end points of sensed R-waves. End points are identified in response to the occurrence of a series of sequential digitized signals which differ from proceeding signals by more than a predetermined amount, and the width of the R-wave is defined as the interval between the first such identified end point associated with a detected R-wave and the last such detected end point associated with the same detected R-wave.

10 Claims, 7 Drawing Sheets

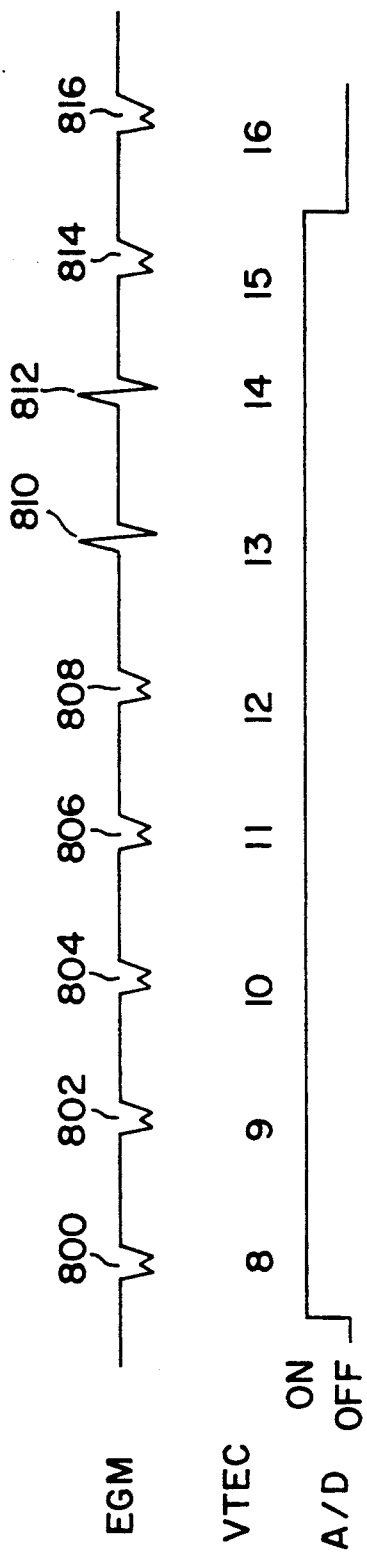
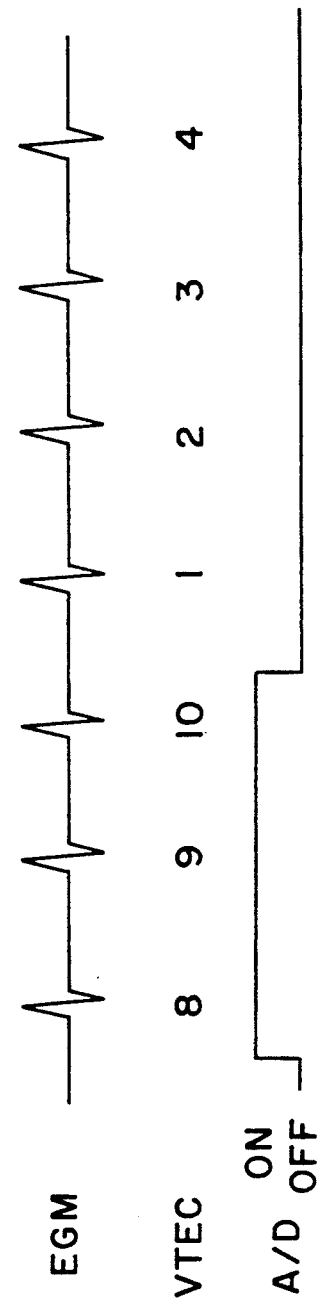
FIG. 5a
FIG. 5b

METHOD AND APPARATUS FOR DISCRIMINATION OF VENTRICULAR TACHYCARDIA FROM SUPRAVENTRICULAR TACHYCARDIA AND FOR TREATMENT THEREOF

BACKGROUND OF THE INVENTION

This invention relates to implantable stimulators generally and more particularly to implantable cardioverters and defibrillators.

Early automatic tachycardia detection systems for automatic implantable cardioverter/defibrillators relied upon the presence or absence of electrical and mechanical heart activity (such as intramyocardial pressure, blood pressure, impedance, stroke volume or heart movement) and or the rate of the electrocardiogram to detect hemodynamically compromising ventricular tachycardia or fibrillation. For example, the 1961 publication by Dr. Fred Zacouto, Paris, France, entitled, "Traitement D'Urgence des Differents Types de Syncopes Cardiaques du Syndrome de Morgangni-Adams-Stokes" (National Library of Medicine, Bethesda, MD) describes an automatic pacemaker and defibrillator responsive to the presence or absence of the patient's blood pressure in conjunction with the rate of the patient's electrocardiogram to diagnose and automatically treat brady and tachyarrhythmias.

Later detection algorithms proposed by Satinsky, "Heart Monitor Automatically Activates Defibrillator", Medical Tribune, 9, No. 91:3, Nov. 11, 1968, and Shuder et al. "Experimental Ventricular Defibrillation with an Automatic and Completely Implanted System", Transactions American Society for Artificial Internal Organs, 16:207, 1970, automatically detected and triggered defibrillation when the amplitude of the R-wave of the electrocardiogram fell below a predetermined threshold over a predetermined period of time. The initial system proposed by Mirowski et al. in U.S. Pat. No. Re 27,757, which similarly relied upon the decrease in the amplitude of a pulsatile right ventricular pressure signal below a threshold over a predetermined period of time, was abandoned by Mirowski et al. in favor of the rate and/or probability density function morphology discrimination as described in Mower et al., "Automatic Implantable Cardioverter-Defibrillator Structural Characteristics", PACE, Vol. 7, November-December 1984, Part II, pp. 1331-1334.

More recently, others have suggested the use of high rate plus acceleration of rate or "onset" (U.S. Pat. No. 4,384,585) with sustained high rate and rate stability (U.S. Pat. No. 4,523,595). As stated in the article "Automatic Tachycardia Recognition", by R. Arzbaecher et al., PACE, May-June 1984, pp. 541-547, anti-tachycardia pacemakers that were undergoing clinical studies prior to the publication of that article detected tachycardia by sensing a high rate in the chamber to be paced. The specific criteria to be met before attempting tachyarrhythmia termination by pacing involved a comparison of the detected heart rate to a preset threshold, such as 150 beats per minute (400 millisecond cycle length) for a preselected number of beats. As stated above, other researchers had suggested the rate of change of rate or suddenness of onset, rate stability and sustained high rate as additional criteria to distinguish among various types of tachyarrhythmias.

In practical applications, a common approach has been to specify discrete rate zones for ventricular fibrillation and ventricular tachycardia, each defined by minimum rates or minimum R—R intervals. However, in some patients, ventricular tachycardia and supraventricular tachycardias including sinus tachycardias may have similar rates that make them difficult to distinguish from one another. For this reason, a more detailed analysis of the electrical waveforms associated with depolarization of the ventricles has often been employed to differentiate among various tachycardias.

SUMMARY OF THE INVENTION

The present invention comprises a method and apparatus for reliable discrimination between ventricular depolarizations resulting from normal and abnormal propagation of the depolarization wavefront through the ventricles by means of a measurement of the width of the sensed R-wave associated with the depolarization. The device embodying the present invention may employ two electrode pairs, one pair used for detection of the occurrence of a ventricular depolarization, one pair used to provide a stored electrogram sample for waveform analysis. Each electrode pair is coupled to circuitry for monitoring electrical signals resulting from the passage of depolarization wavefronts.

The electrode pairs may include a common electrode between the two pairs, or may comprise four separate electrodes. Alternatively, only a single electrode pair may be employed for both R-wave detection and waveform analysis. Identification of the time of occurrence of an R-wave is used to set a time window for storage of a digitized recording of the R-wave for waveform analysis. The time window preferably extends from a time prior to R-wave detection to a point following R-wave detection, and includes a sufficient time (e.g. 50 ms or greater) to assure that the entire R-wave is recorded.

After detection of an R-wave and the expiration of the associated time window, the device embodying the present invention examines the digital values stored during the time window and determines the width of the R-wave, using a only single pass through the stored data to identify both the start and end points for the R-wave. The method of waveform analysis performed by the present invention provides a particularly economical use of processor time, and requires relatively few mathematical calculations. While the resultant width measurement is not necessarily extremely accurate, it nonetheless provides a measurement of relative width which is adequate to distinguish R-waves of sinus origin or of nodal origin from R-waves of ventricular origin. The measured width over a series of detected depolarization wavefronts is used in conjunction rate based analysis is to distinguish among various types of tachycardias.

The present invention is intended to be used in conjunction with an implantable pacemaker/cardioverter/defibrillator which provides therapies for detected ventricular tachycardia and detected ventricular fibrillation. For example, in response to detection of a ventricular tachycardia, the device may provide burst pacing, overdrive pacing or some other antitachycardia pacing regimen. Alternatively, it may provide a low to high energy cardioversion pulse. Typically, in response to detection of fibrillation, the device will provide a defibrillation pulse at an amplitude significantly higher than a cardioversion pulse.

It is believed that the invention is optimally embodied in a device which is capable of differentiating between various types of tachycardia, particularly for use in a device intended to identify sinus and supraventricular tachycardias and to distinguish them from ventricular tachycardia and ventricular fibrillation, and which provides an antitachycardia therapy at least in response to detection of ventricular tachycardia.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which:

FIGS. 5a and 5b are simulated EGM strips and associated timing information illustrating the operation of the software diagrammed in FIG. 4.

DETAILED DESCRIPTION OF THE PREFERRED EMBODIMENTS

Figure 1:
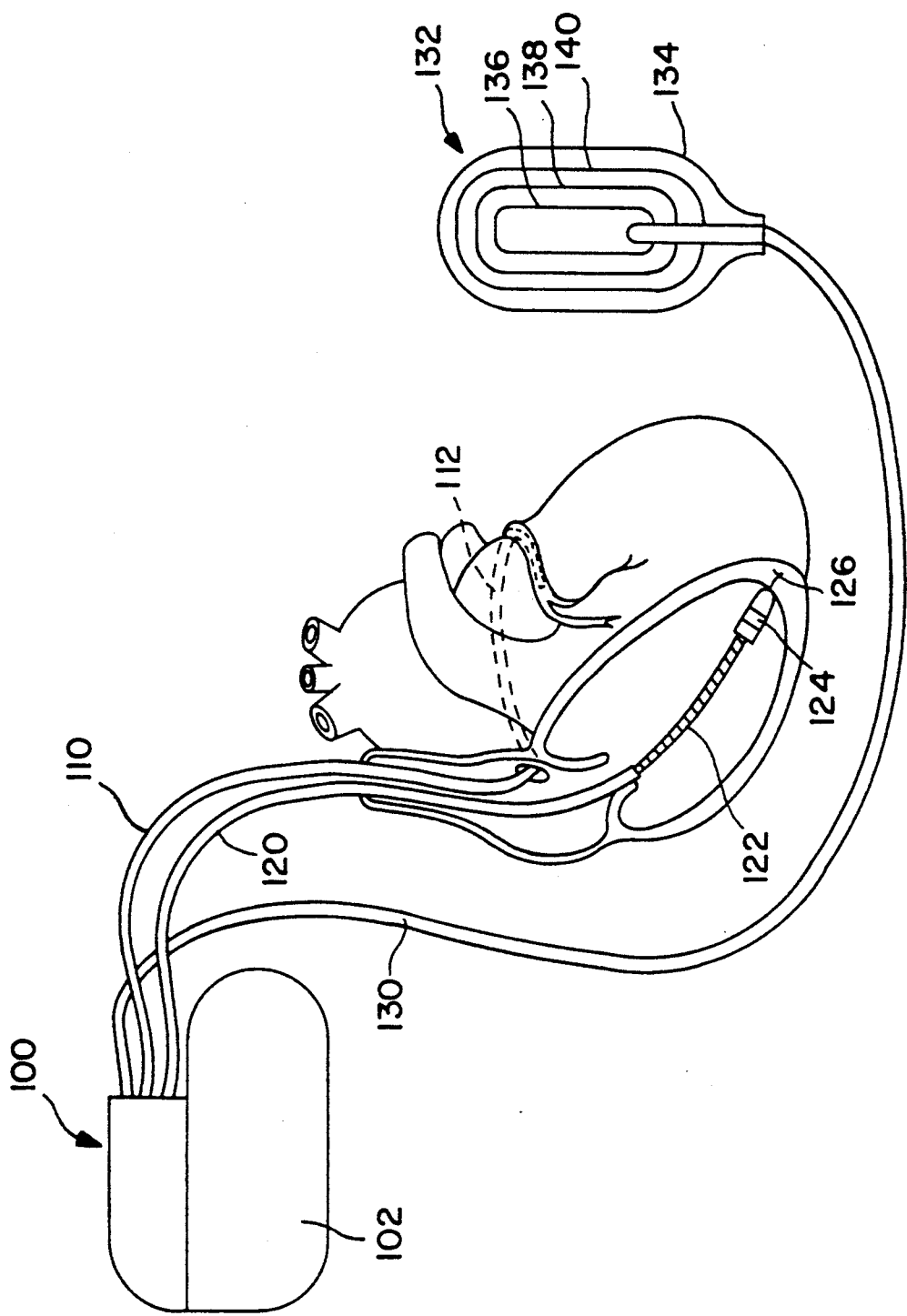
FIG. 1 illustrates a transvenous/subcutaneous electrode system in conjunction with a pacemaker/cardioverter/defibrillator embodying the present invention.

FIG. 1 illustrates an implantable pacemaker/ cardioverter/defibrillator 100 and its associated lead system, as implanted in and adjacent to the heart. As illustrated, the lead system comprises a coronary sinus lead 110, a right ventricular lead 120, and a subcutaneous lead 130. The coronary sinus lead is provided with an elongated electrode located in the coronary sinus and great vein region at 112, extending around the heart until approximately the point at which the great vein turns downward toward the apex of the heart. The right ventricular lead 120, includes an elongated defibrillation electrode 122, a ring electrode 124, and helical electrode 126, which is screwed into the tissue of the right ventricle at the right ventricular apex.

Leads 110 and 120 may correspond to the leads disclosed in allowed U.S. Patent Ser. No. 07/284,955 by Bardy for an "Endocardial Defibrillation Electrode System", filed Dec. 15, 1988 and incorporated herein by reference in its entirety. A subcutaneous lead 130 is also illustrated, implanted subcutaneously in the left chest. Lead 130 includes a large surface electrode pad 132, carrying elongated electrode coils 136, 138 and 140. Electrode 132 may correspond to the electrode illustrated in allowed U.S. patent application Ser. No. 07/376,730, by Lindemans et al. for a Medical Electrical Lead, filed Jul. 7, 1989 and incorporated herein by reference in its entirety.

In conjunction with the present invention, the lead system illustrated provides numerous electrodes which may be used to detect electrical activity in the ventricles. For example, ring electrode 124 and tip electrode 126 may be used to detect the occurrence of an R-wave and ring electrode 124 and subcutaneous defibrillation electrode 132 may be used to provide the EGM signal stored in response to R-wave detect. Alternatively, electrodes 124 and 126 may be used for both R-wave detection and as a source for the stored digitized EGM signal used for width measurement. Other electrode configurations may also be employed.

Figure 2:
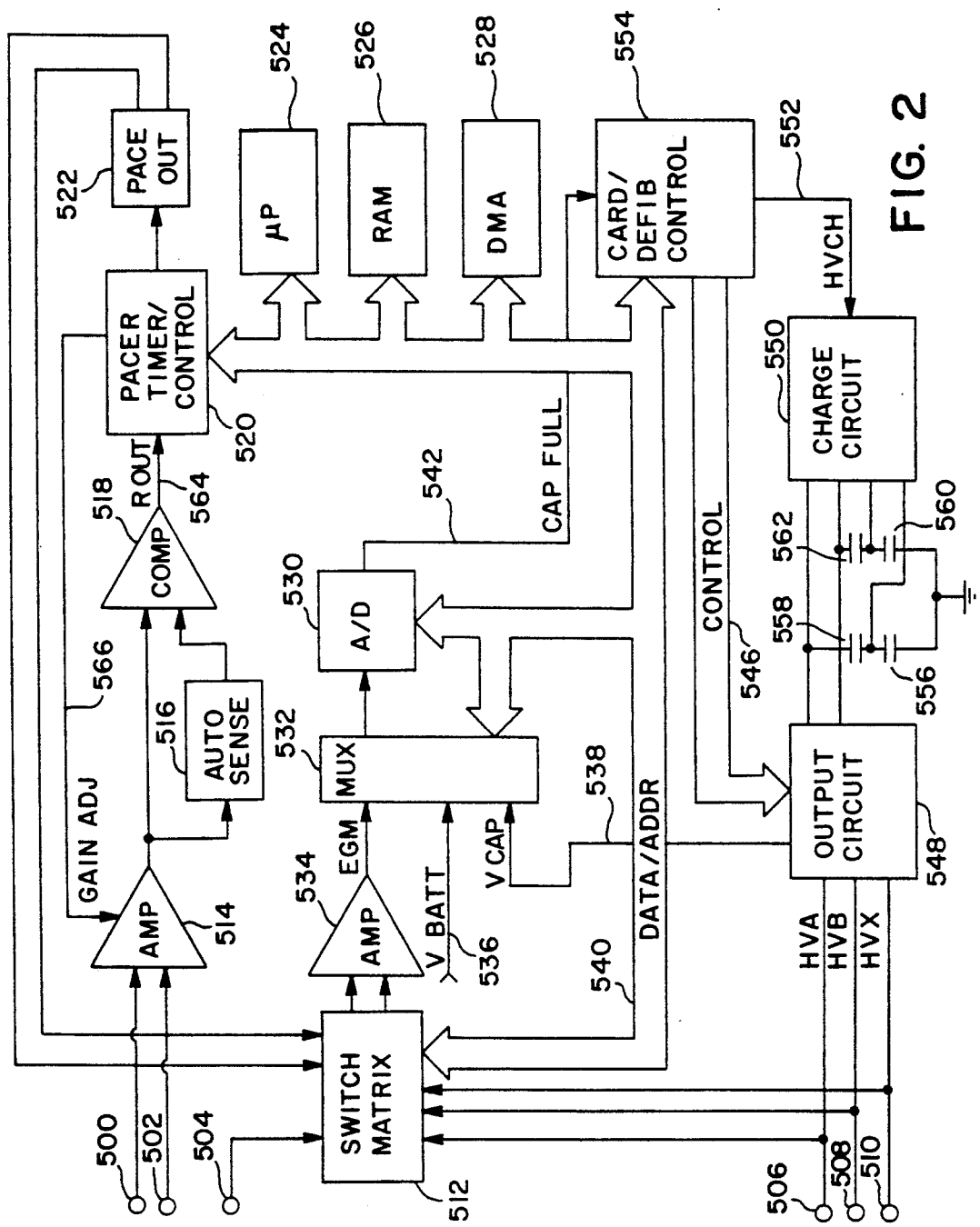
FIG. 2 is a schematic block diagram illustrating the structure of one embodiment of an implantable pacemaker/cardioverter/defibrillator in which the present invention may be embodied.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21, 1990, all of which are incorporated herein by reference in their entireties.

The device is illustrated as being provided with six electrodes, 500, 502, 504, 506, 508 and 510. Electrodes 500 and 502 may be a pair of electrodes located in the ventricle, for example, corresponding to electrodes 124 and 126 in FIG. 1. Electrode 504 may correspond to a remote, indifferent electrode located on the housing of the implantable pacemaker/cardioverter/defibrillator. Electrodes 506, 508 and 510 may correspond to the large surface area defibrillation electrodes located on the ventricular, coronary sinus and subcutaneous leads illustrated in Figure or to epicardial defibrillation electrodes.

Electrodes 500 and 502 are shown as hard-wired to the R-wave detector circuit, comprising bandpass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned, copending U.S. patent application Ser. No. 07/612,760, by Keimel, et al, filed Nov. 15, for an Apparatus for Monitoring Electrical Physiologic Signals, incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present invention.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp 67–72, 1978, incorporated herein by reference in its entirety.

In the context of the present invention, it is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1–3 seconds following adjustment of the sensing threshold equal to 70–80% of the amplitude of a detected spontaneous R-wave. The invention may also be practiced in conjunction with more traditional R-wave sensors of the type comprising a band pass amplifier and a comparator circuit to determine when the bandpassed signal exceeds a predetermined, fixed sensing threshold.

Switch matrix 512 is used to select which of the available electrodes make up the second electrode pair for use in conjunction with the present invention. The second electrode pair may comprise electrode 502 or 500 in conjunction with electrode 504, 506, 508 or 510, or may comprise other combinations of the illustrated electrodes, including combinations of the large surface defibrillation electrodes 506, 508, 510. Selection of which two electrodes are employed as the second electrode pair in conjunction with R-wave width measurement function is controlled by the microprocessor 524 via data/address bus 540. Signals from the selected electrodes are passed through bandpass amplifier 534 and into multiplexer 532, where they are converted to multibit digital signals by A/D converter 530, for storage in random access memory 526 under control of direct memory address circuit 528. Microprocessor 524 analyzes the digitized EGM signal stored in random access memory 526 to determine the width of the stored R-wave.

For example, the microprocessor 524 may analyze the EGM stored in an interval extending from 100 milliseconds previous to the occurrence of an R-wave detect signal on line 564, until 100 milliseconds following the occurrence of the R-wave detect signal in order to determine the width of the stored R-wave.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of bandpass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including antitachycardia pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the width measurement function.

Microprocessor 524 operates as an interrupt driven device, and responds to interrupts from pacer timing-/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an antitachyarrhythmia pacing regimen is desired, appropriate timing intervals for controlling generation of antitachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters to in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in copending, commonly assigned U.S. patent application Ser. No. 07/612,761, by Keimel, for an Apparatus for Detecting and Treating a Tachyarrhythmia, filed Nov. 15, 1990 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed. Similarly known circuitry for controlling the timing and generation of antitachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In modern pacemaker/cardioverter/defibrillators, the particular antitachycardia and defibrillation therapies are programmed into the device ahead of time by the physician, and a menu of therapies is typically provided. For example, on initial detection of tachycardia, an antitachy cardia pacing therapy may be selected. On redetection of tachycardia, a more aggressive antitachycardia pacing therapy may be scheduled. If repeated attempts at antitachycardia pacing therapies fail, a higher level cardioversion pulse therapy may be selected thereafter. Prior art patents illustrating such preset therapy menus of antitachyarrhythmia therapies include the above-cited U.S. Patent No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known antitachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multielectrode, simultaneous pulse regimen or a multielectrode sequential pulse regimen. Monophasic or biphasic pulses may be generated. One example of circuitry which may be used to perform this function is set forth in commonly assigned copending patent application Ser. No. 07/612,758, filed by Keimel, for an Apparatus for Delivering Single and Multiple Cardioversion and Defibrillation Pulses, filed Nov. 14, 1990, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

As discussed above, switch matrix 512 selects which of the various electrodes are coupled to band pass amplifier 34. Amplifier 34 may be a broad band pass amplifier, having a band pass extending for approximately 0.5 to 200 hertz. The filtered EGM signal from amplifier 534 is passed through multiplexer 532, and digitized in A-D converter circuitry 530. The digitized EGM data is stored in random access memory 526 under control of direct memory address circuitry 528. Preferably, a portion of random access memory 526 is configured as a looping or buffer memory which stores at least the preceding several seconds of the EGM signal.

The occurrence of an R-wave detect signal on line 564 is communicated to microprocessor 524 via data-/address bus 540, and microprocessor 524 notes the time of its occurrence. If the width measurement function is activated, microprocessor 524 waits 100 milliseconds or other physician selected interval following the occurrence of the R-wave detect signal, and thereafter transfers the most recent 200 milliseconds or other physician selected interval of digitized EGM stored in the looping or buffer memory portion of the random access memory circuit 526 to a second memory location, where the contents may be digitally analyzed to determine the width of the stored R-wave. The transferred 200 milliseconds of stored EGM corresponds to a time window extending 100 milliseconds on either side of the R-wave detect signal. Window sizes in any case should be sufficient to allow measurement of the width of detected R-waves. Preferably, the window should expire during the blanking period following R-wave detection. For purposes of the present invention, a sampling rate of 256 Hz should be sufficient.

The microprocessor also updates counters which hold information regarding the R—R intervals previously sensed. The counters are incremented on the occurrence of measured R—R intervals falling within associated rate ranges. These rate ranges may be defined by the programming stored in the RAM 526.

A first rate range may define a minimum R—R interval used for fibrillation detection, referred to as "FDI". The associated VF count preferably indicates how many of a first predetermined number of the preceding R—R intervals were less than FDI.

A second rate range may include R—R intervals less than a lower tachycardia interval "TDI", and the associated VT count (VTEC) is incremented in response to an R—R interval less than TDI but greater then FDI, is not affected by R—R intervals less than FDI, and is reset in response to R—R intervals greater than TDI.

Optionally, the device may include a third rate range including R—R intervals greater than the FDI interval, but less than a fast tachycardia interval (FTDI) which is intermediate the lower tachycardia interval (TDI) and the lower fibrillation interval (FDI). In devices which employ this optional third rate range, it is suggested that the width criterion be employed only in conjunction with detection of rhythms within the lower rate range, e.g., sequences of intervals between TDI and FTDI.

For purposes of the present example, the counts may be used to signal detection of an associated arrhythmia (ventricular fibrillation, fast ventricular tachycardia or lower rate ventricular tachycardia) when they individually or in combination reach a predetermined value, referred to herein as "NID's" (number of intervals required for detection). Each rate zone may have its own defined count and NID, for example "VFNID" for fibrillation detection and "VTNID" for ventricular tachycardia detection or combined counts may be employed.

These counts, along with other stored information reflective of the previous series of R—R intervals such as information regarding the rapidity of onset of the detected short R—R intervals, the stability of the detected R—R intervals, the duration of continued detection of short R—R intervals, the average R—R interval duration and information derived from analysis of stored EMG segments are used to determine whether tachyarrhythmias are present and to distinguish between different types of tachyarrhythmias. Such detection algorithms for recognizing tachycardias are described in the above cited U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7-10, 1986, IEEE Computer Society Press, pages 167-170, also incorporated by reference in its entirety herein. However, other criteria may also be measured and employed in conjunction with the present invention.

For purposes of the present invention, the particular details of implementation of the rate/R—R interval based VF/FVT/VT detection methodologies are not of primary importance. However, it is required that the VF/FVT/VT rate detection methodologies employed by the device allow identification and detection of rhythms in the rate range in which operation of the R-wave width measurement function is desired. It is also important that the width measurement function be initiated far enough in advance of the point at a heart rhythm within the desired rate range can be detected to allow for measurement of the required number of values of R-wave width before the heart rhythm is diagnosed positively as being within the desired rate range. In this fashion, the processed width values will be available for use immediately in response to the rate criteria being met. Diagnosis of the detected arrhythmia and a selection of the therapy to be delivered can likewise be done immediately in response to the rate based criteria being met.

For example, the width measurement function may appropriately be initiated and measurement of R-wave widths begun at the time the VT count (VTEC) equals VTNID, minus "n", where "n" is the number of measured values of R-wave width employed to determine whether the width criterion is met. The same result may also be accomplished by initiating width measurement of in response to the VT count reaching a different predetermined value substantially less than VTNID.

Figure 3:
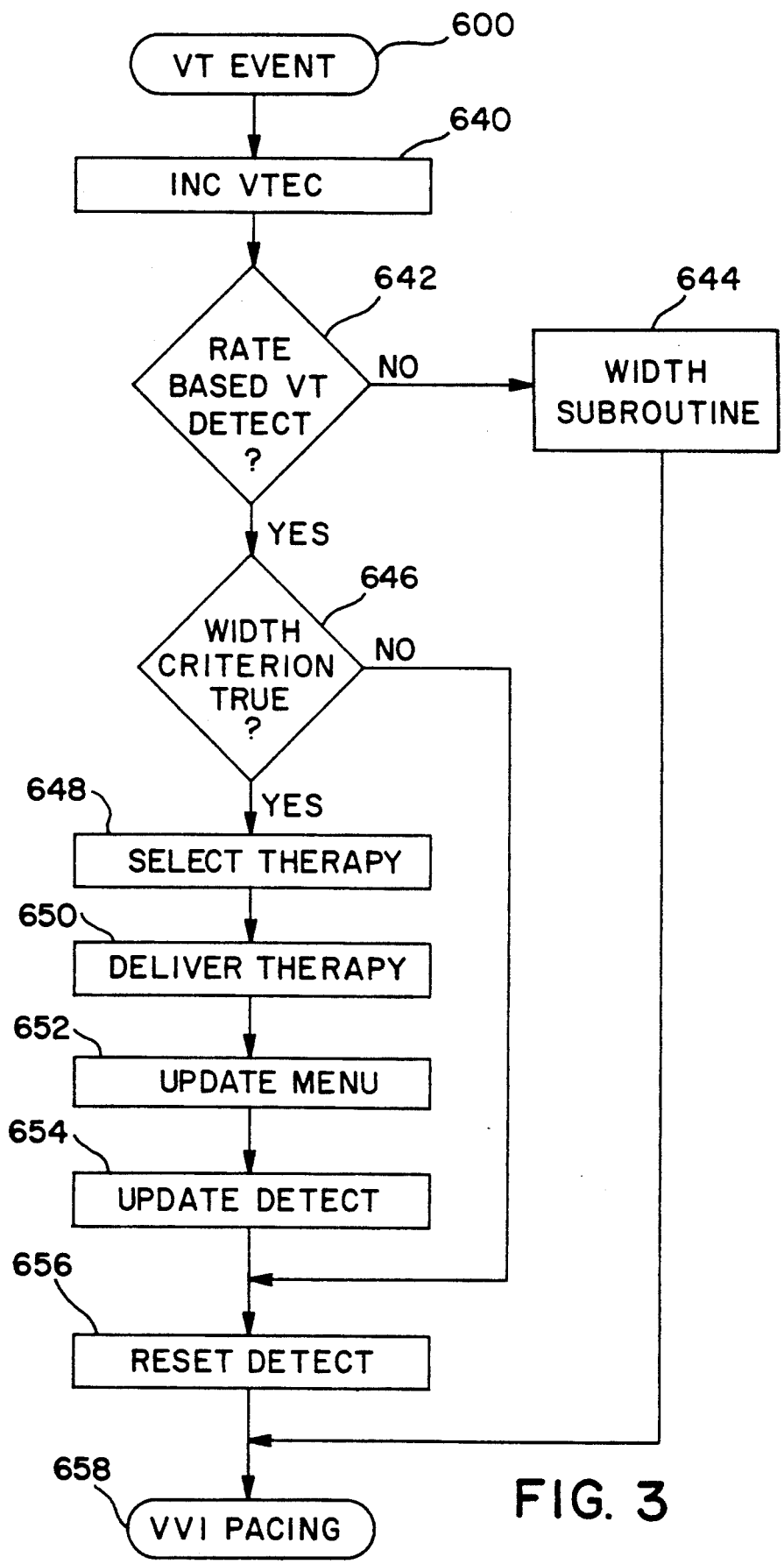
FIG. 3 is a functional flow chart illustrating the overall operation of the tachycardia detection function and its interrelation with the R-wave width measurement function provided by the present invention, as embodied in a microprocessor based device as illustrated in FIG. 2.

FIG. 3 is a flow chart representing the operation of the device illustrated in FIG. 2, in conjunction with the R-wave width measurement function. FIG. 3 is intended to functionally represent that portion of the software employed by microprocessor 524 (FIG. 3) which implements the width measurement function and which employs the width criterion in conjunction with VT detection. This portion of the software is executed in response the sensing of a ventricular depolarization at 600 which qualifies as a ventricular tachycardia event, which, by virtue of its timing is appropriate for incrementing the VTEC at 640.

This value (VTEC) is the ventricular tachycardia count discussed above, which is compared VTNID.

It is envisioned that onset and stability requirement are optional in a device employing the present invention, and preferably are made available as programmable options, which may be deleted by external programmer command. If included, it is believed preferable that the onset criteria be required to be met prior to initiating counting of VTEC, and that once met, the criteria will remain satisfied until detection of tachycardia termination. Thus, onset is not intended to be a detection criteria required for redetection of tachycardia, following initial detection. In the flow chart of FIG. 3, the width criterion should also be understood to be used only for use both in initial detection of tachycardia and in redetection of tachycardia. This reflects a presumption that following initial detection of ventricular tachycardia, absent a proven return to normal heart rhythm (termination detect), subsequent high ventricular rates should be presumed to be ventricular in origin. The stability criterion, on the other hand, is believed to be appropriate for use both in initial detection of tachycardia and in redetection of tachycardia.

In the event that the rate based criteria for tachycardia detection are not met at 642, the width measurement subroutine is performed at 644. This subroutine is described in detail in FIG. 4. For purposes of FIG. 3, it is only important to understand that the width measurement subroutine determines whether the width of at least a predetermined number of the preceding series of R waves is indicative of a ventricular tachycardia. If so, the width criteria is met. Meeting the width criteria is an absolute prerequisite in the flow chart of FIG. 3 to delivery of a ventricular antitachycardia therapy.

In the event that the width criterion is met at 646, the occurrence of ventricular tachycardia is detected and the therapy menu is examined at 648 to determine the presently scheduled antitachy therapy. The scheduled therapy is delivered at 650, the tachycardia menu is updated at 652 to reflect the delivery of the therapy at 650, and the detection criteria are updated at 654 to reflect the fact that a tachycardia has previously been detected and not yet terminated. Detection counts are reset at 656, and the device returns to bradycardia pacing until redetection tachycardia or fibrillation or detection of termination of tachycardia.

Detection of termination of tachycardia may be accomplished by means of detection of a predetermined number of sequential R—R intervals indicative of normal heart rate. Normal heart rat may be defined as R—R intervals greater than TDI.

Figure 4:
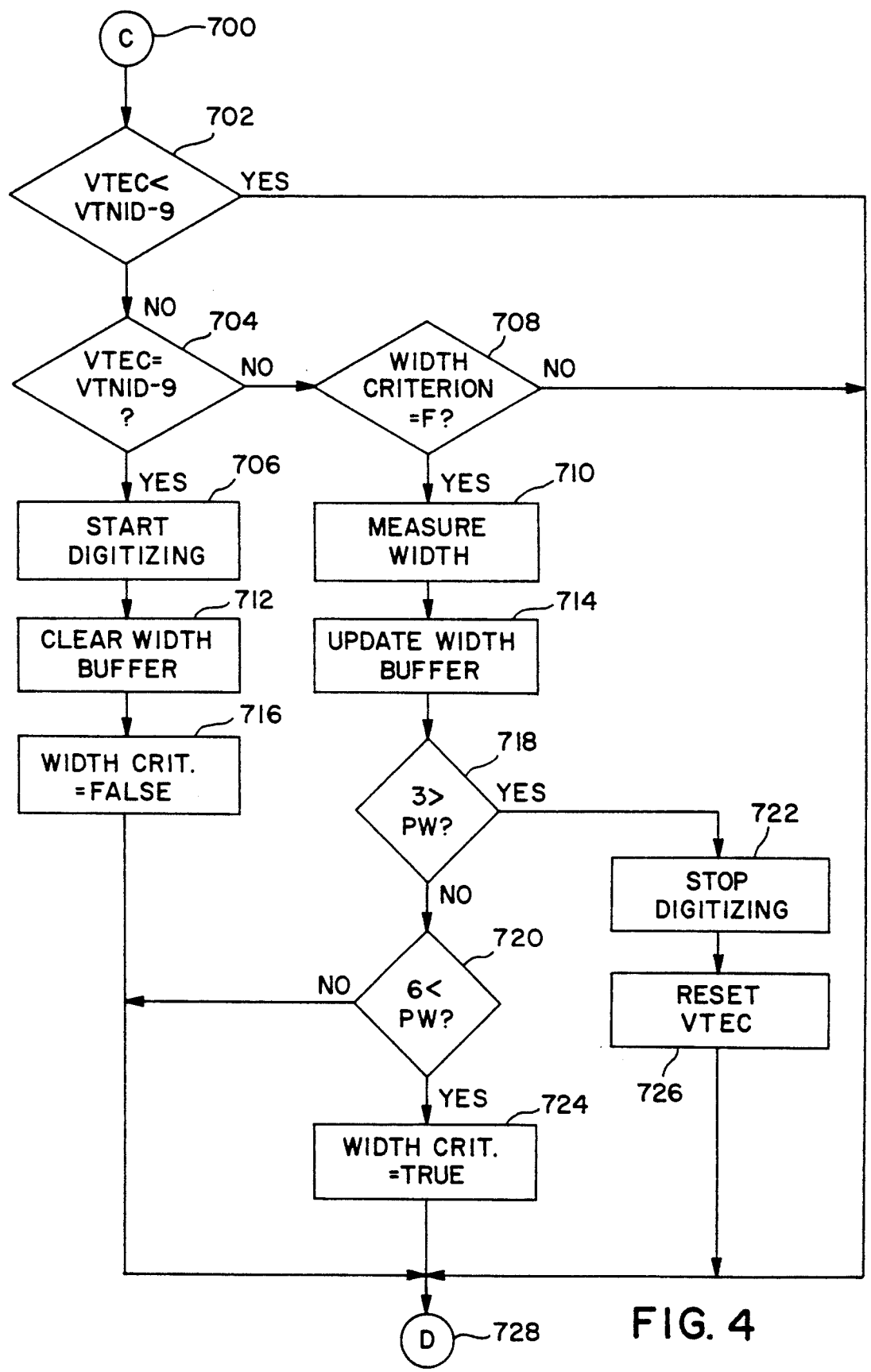
FIG. 4 is a functional flow chart illustrating the operation of software for implementing the method by which the present invention determines whether sensed R-waves meet criteria indicative of a ventricular tachycardia.

FIG. 4 is a flow chart representing the portion of the software directed to determining whether the width criteria has been met. In general, it corresponds to the "width subroutine" box 644 illustrated in FIG. 3. This portion of the software is entered in response to incrementation of the ventricular tachycardia count (VTEC), during an initial detection sequence.

At 702, the microprocessor checks to determine whether a ventricular count (VTEC) is less than VTNID−9. If so, this indicates that the detection sequence is at an early enough stage that the width measurement function need not be activated.

At 704, the microprocessor checks to determine whether VPEC equals VTNID−9. If so, this signifies that it is the proper time int he detection sequence to activate the width measurement function, and storage of digitized R-waves associated with V sense detects in begun at 706. The width buffer is cleared at 712. In the context of the present invention, the width buffer is a count, similar to the fibrillation event buffer, indicative of how many out of a preceding predetermined number of measured R-waves widths exceed a minimum width threshold. For example, in the specific flow chart illustrated in FIG. 4, the width buffer is a record of how many of the preceding eight digitized R-waves had widths in excess of a minimum R-wave width. At 716, a width criteria flag is set at false, to indicate that the width criteria is not yet met, and the device returns to the flow chart of FIG. 3, at box 646. Because at the point of initial activation of the width measurement function, VTEC will not be equal to VTNID, the device thereafter returns to bradycardia pacing until either tachycardia is detected or the termination criteria is met.

In the event that VTEC is greater VTNID−9, the width criteria is checked at 708 to determine whether it is true or false. For purposes of the flow chart illustrated in FIG. 4 and the simulated EKG and associated function charts of FIG. 5, the width criteria may be satisfied when six of the previous eight digitized R-waves exceed the minimum width threshold. The width criteria may be set false either on initial activation of the measurement function, as illustrated at 716, or in response to the occurrence of three or more of the previous eight R-waves having a pulse width of less than the minimum width threshold.

The operation of the remainder of the flow chart is best considered in conjunction with FIGS. 5a and 5b.

FIG. 5a illustrates the circumstance in which the width criteria is met. In this case, VTNID is presumed to be equal to 16 and the width criteria is presumed to be satisfied in the event that six out of the preceding eight measured R-waves exceed the minimum width threshold. As illustrated at 800, an R-wave occurs where it resulting in VTEC being incremented to a count of eight. Because the previous R-wave caused incrementation of VTEC to equal VTNID−9, the A-D conversion function had been activated, and digitization of ht 200 millisecond windows associated with R-wave detection begins with R-wave 100. R-waves 800, 802, 804, 806 and 808 all are illustrated as broad R-waves of ventricular origin, and all are presumed to exceed the minimum width threshold. R-waves 810 and 812 are shown as being narrow R-waves, and are presumed to fall below the minimum width threshold. R-wave 814 is again a wide R-wave, so that the fibrillation event buffer now reflects the occurrence of six out of the previous eight R-waves exceeding the width threshold.

Turning back tot he flow chart of FIG. 4, assuming that at 710, the width of R-wave 814 has just been measured, and the width buffer has been updated at 714 to reflect that six of the previous eight R-waves exceeded the minimum width threshold. At 718, the microprocessor checks to determine whether three of the previous eight R-waves have been found to be narrower than the minimum width threshold, which in the case of FIG. 5a, is untrue. At 720 therefore, the microprocessor again checks the fibrillation event buffer to determine whether six of the previous eight R-waves have been greater than the minimum width threshold. Because with R-wave 814, this condition will be met, the width criteria is set as true at 724. On subsequent occurrence of a ventricular event count equal to VTID, therefore, the scheduled ventricular antitachycardia therapy will be delivered.

In FIG. 5b, we see a simulated EGM strip illustrating the circumstance in which the width criteria is not met. Again, the first R-wave, 818, is shown as incrementing the VT event counter to eight. Because the digitization function was activated in response to the previous R-wave (VTEC=VTNID−9), R-wave eight and subsequent R-waves nine and ten are digitized and checked to determine whether their width exceeds the minimum width threshold. In each case, as illustrated, it is assumed that the width of the R-waves does not exceed the minimum width threshold. Therefore, after R-wave 822, at 718 the condition of three of the previous eight R-waves being less than the minimum width threshold will be true, causing the digitizing function to be disabled at 722, and the Thus, subsequent R-waves 824, 826, 828 and 830 cause the ventricular tachycardia event count to begin counting anew. As illustrated in FIG. 5b, however, the onset and stability requirements remain satisfied, and incrementation of VTEC begins immediately. There is no need to satisfy the requirement of onset detection again as a prerequisite to incrementing the ventricular tachycardia count.

Figure 6:
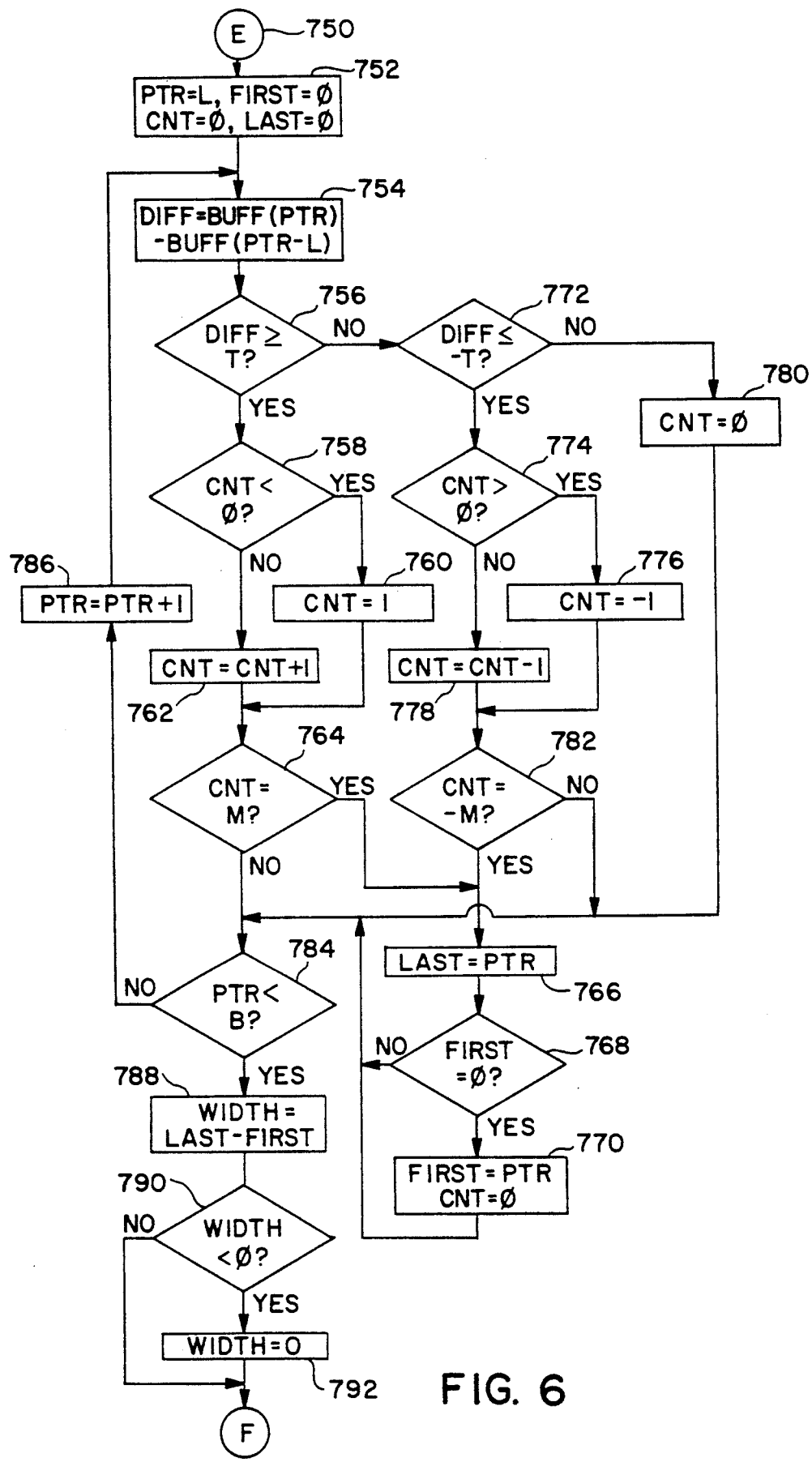
FIG. 6 is a functional flow chart illustrating the operation of software for implementing the method by which the present invention measures the width of an individual R-wave.
Figure 7:
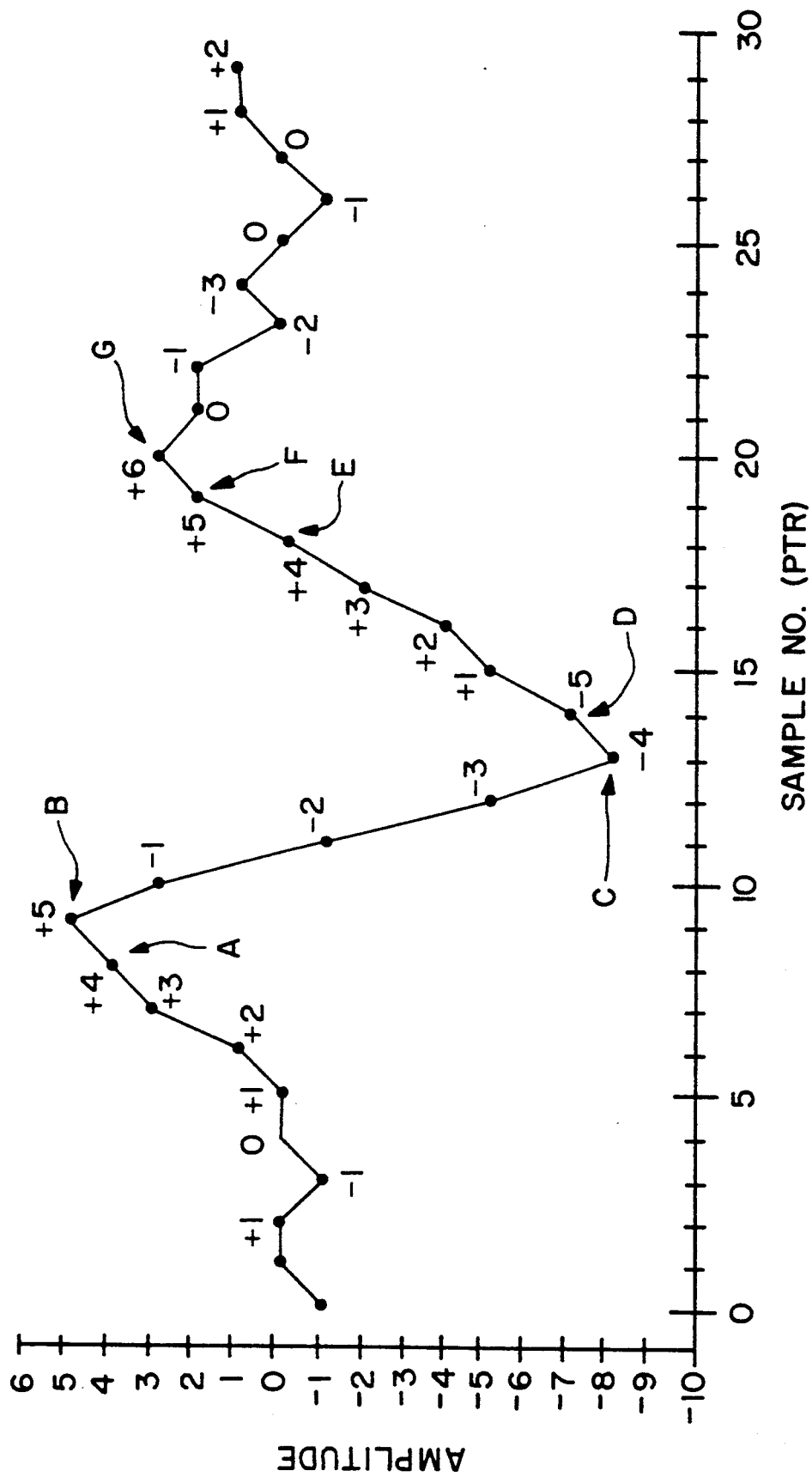
FIG. 7 is a graph which illustrates the measurement of the width of a stored, digitized R-wave using the present invention using the software diagrammed in FIG. 6.

FIG. 6 is a flow chart of that portion of the software dedicated to measurement of the width of individual stored R-waves. FIG. 6 thus corresponds to function block 710 in FIG. 4. The operation of the software illustrated in FIG. 6 can best be understood in conjunction with the diagram of FIG. 7, illustrating the measurement of the width of an individual digitized R-wave. FIG. 7 represents a simplified and shortened data set in which only 30 samples are taken. However, the width measurement methodology applied to FIG. 7 is equally applicable to larger data sets.

Detection of the beginning and end points of the R-wave is accomplished by taking each stored sample and sequentially comparing it to one or more preceding samples. In the simplest application of this methodology, each sample could be compared to the immediately preceding sample. In this case, the methodology would employ a "book back" parameter equal to parameter equal 2 is employed. Thus, each digitized sample is compared to the value two samples back. On occurrence of a measured difference of greater than or less than a predetermined value, a positive or negative count is incremented. When the positive or negative count equals a predetermined value, in this case four, a continued segment of high slope is identified. The methodology of width measurement identifies all segments of high slope, and identifies the initial segment of high slope as the beginning point of the R-wave, and the final segment of high slope as the termination point of the R-wave. This process can be understood in more detail by an examination of the flow chart of FIG. 6.

The flow chart of FIG. 6 is entered at 750 following the conditional block at 708 in FIG. 4. The pointer is set equal to the look back parameter (PQR=L), to define the initial digital sample that will be considered. A flag "first" is set to zero, a running count (CNT) is set to zero, and a second flag "last" is also set to zero. The function of these counts and flags will be discussed in more detail below.

At 754, the sample and buffer at "PTR" is compared to the sample in the buffer at "PTR−L", and its difference is determined. As illustrated in FIG. 7, the first sample is at PTR=0. Therefore, the first sample considered is at PTR =2, which comprises the third data sample. In the event that the measured difference exceeds "T" at 756, the value of the running count (CNT)

is checked at 758 to determine whether it was less than zero, which would indicate a previous segment of negative slope, and thus a negative running count. If CNT is less than zero, CNT is set to 1 at 760 indicating the beginning of a section of positive slope. In the event that CNT is not less than zero, CNT is set to CNT plus 1 at 762.

The operation of this much of the flow chart is illustrated by the first three data points in FIG. 7. The third data point is PTR=2 has associated therewith a value "plus 1", which corresponds to the value of CNT at that point. Looking back two samples, we see that the value of the sample at PTR=2 is one greater than the value of the sample at PTR −L (PTR=0). Therefore, the value of CNT is incremented to +1 at PTR=3.

Returning to FIG. 3, in the event that the sample at PRT does not exceed the value of the sample two samples previous thereto at 756, the value of the sample at PTR is compared again with the sample two samples previous to determine whether it is less than that previous sample by greater "T". If so, the value of CNT is checked at 744 to determine whether it is greater than zero, which would indicate a previous section of positive slope. If so, the value of CNT is set to negative one at 776, indicating the beginning of a section of negative slope. If not, CNT is set to CNT−1 at 778.

This portion of the software is reflected by examining the sample at PRT=3, in FIG. 7. Associated therewith is a value of "−1" indicating the beginning of a section of negative slope as per the flow chart of FIG. 6. Because the value of the sample at PTR=4 is one less than the value of the sample at PRT=2, the value of CNT is set to −1.

Returning to the flow chart of FIG. 6, in the even that the difference between the sample presently indicated by PTR is less than "T" different from the sample two samples preceding it, the value of CNT is set equal to zero at 780. This portion of the operation of the flow chart is reflected by an examination of the digitized value stored at PTR=4 in FIG. 7. Associated therewith is a value of "0" reflecting the fact that the value stored at PTR=4 is the same as the value at PRT=2.

In the fashion described above, the running value of CNT is either incremented, decremented, or set to zero. In the event that CNT has been incremented, the microprocessor checks at 764 to determine whether CNT is greater than or equal to M. M, in this case, is a preset value indicative of the number of successive samples reflective of increasing slope, required to detect an R-wave edge, either leading or trailing. As illustrated in FIGS. 6 and 7, the value of "M" is equal to 4. In the event that the value of CNT is decremented, it is compared with −M at 782 to determine whether four successive samples have occurred indicative of continuous significant negative slope.

In the event that either CNT is equal to M or M, the value of "last" is set equal to the present value of the pointer (PTR) at 766. The operation of this portion of the software can be understood by examining the samples at PTR=8 and 9. At PTR=8, the associated value of CNT is equal to +4. Therefore, this point, labeled as "A" in FIG. 7 reflects the first time at which CNT is greater than or equal to M. Thus, 8 will be the initial value of "last", at 766 (FIG. 6). At 768, the value of "first" is checked to determine whether it is still set at zero, which would indicate no prior R-wave edge detects. If "first" is equal to zero, then "first" is set equal to the present value of PTR at 770, and CNT is reset to zero. Returning to the diagram of FIG. 7, we find therefore, that "first" and "last" will both initially be set equal to 8, in response to the sample labelled as "A". The sample at PTR=9, labelled "B" will result in a new value for "last" equal to nine.

Following the analysis of each stored sample according to the criteria discussed above, the pointer is compared to "B" at 784, which is the length of the buffer. If the pointer is equal to the buffer length (in this case 29) this indicates that all samples have been examined. If not, the value of the pointer is incremented at 786, and the next sample is examined.

If all samples have been examined, the value of "first" is subtracted from the value of "last" to determine the width at 788. If the width as calculated is less than zero, at 790, the width is set equal to zero at 792. Otherwise, the value of the width remains as calculated, and is then compared against the minimum width criteria, and the width buffer is updated at 714, as discussed in conjunction with FIG. 4.

In FIG. 7, it can be seen that the value of first will be set only one in response to the data sample labeled "A" occurring at PTR equals 8. The value of "last" will be reset a number of times including at the data points labeled "B", "C", "D", "E", "F", and "G". Because "G" occurs at PTR=20, the width of the R-wave illustrated in FIG. 7 will be equal to 20−8 or 12. This value can be compared to a predetermined value indicative of the desired minimum width criteria. Of course, the specific numbers employed for the minimum width criteria will depend upon the sampling frequency. However, generally, it is desirable that a minimum width threshold of 100 to 150 milliseconds is believed appropriate.

The width measurement methodology described in conjunction with FIGS. 6 and 7 allows for identification of the beginning and end points of the R-wave with a reasonable degree of accuracy, while requiring only a single, unidirectional pass through the data stored in the buffer. As illustrated, this pass through the data occurs from the first stored sample to the last. However, the method may as easily be applied from the last stored sample to the first.

While the methodology disclosed does result in some asymmetry with regard to the detection of the start point and endpoint of the R-wave, it nonetheless provides an adequate measurement of pulse width for purposes of distinguishing between R-waves of ventricular origin and R-waves of nodal or sinus origin. Therefore, the methodology of R-wave measurement employed in the present invention is believed particularly valuable in context of an implanted device where processing time and processing operations need to be kept to a minimum in order to maximum battery life.

It should be recognized that although the disclosed embodiment deals with fibrillation and tachycardia in the lower chambers or ventricles of the heart, the invention may possibly be usefully practiced in the context of the upper chambers or atria of the heart, which are also prone to tachycardia and fibrillation in some patients. In addition, while the therapies discussed in conjunction with the disclosed embodiment generally relate to delivery of electrical pulses, it should be understood that the invention may be usefully practiced in conjunction with any device adapted to deliver differing therapies for tachycardia and fibrillation, including drug therapies, non-pulsatile electrical therapies, and any other such therapies as may be implemented in such devices as their development progresses, whether applied directly to the heart or systemically.

Similarly, it should be understood that the width measurement function of the present invention, while particularly adapted for use in or in conjunction with an implantable cardioverter/defibrillator may also in some cases be usefully practiced in conjunction with a non-implantable device, in a device which, for example only treats fibrillation or only treats tachycardia, or even in a device adapted primarily for diagnostic purposes.

In conjunction with above application, we claim:

1. A cardioverter, comprising:
   treatment means for delivering a therapy to a patient's heart to treat ventricular tachycardia; means for sensing electrical signals from the ventricle of said patient's heart;
   detection means, coupled to said sensing means for detecting the occurrence of a depolarization of the ventricle of said patient's heart and for issuing an R-wave signal indicative thereof;
   digitizing means for converting said electrical signals from the ventricle of said patient's heart to digital signals indicative of the magnitude of said electrical signals and for storing said digital signals sequentially;
   windowing means responsive to said R-wave signal for defining a time window extending from a point in time prior to said R-wave signal until a point in time following said R-wave signal; and
   analysis means responsive to said R-wave signal for analyzing the said digital signals stored in the said time window defined in response to the occurrence of said R-wave signal, said analysis means in turn comprising:
      difference measuring means for sequentially scanning through the said digital signals stored during a said time window in a first direction and for measuring the difference between individual ones of said stored digital signals and others of said stored digital signals to determine whether said measured differences exceed a predetermined threshold;
      counting means for counting the number of sequential ones of said difference measurements exceeding said predetermined threshold and for generating an endpoint signal each time said number of said difference measurements exceeding said predetermined threshold reaches a predetermined count;
      width measurement means responsive to said counting means for measuring an interval between a first said endpoint signal to occur during said scanning and a last said endpoint signal to occur during said scanning to provide an R-wave width measurement; and
      ventricular tachycardia detection means responsive to said width measurement for detecting the occurrence of a ventricular tachycardia and for triggering delivery of said therapy.

2. A cardioverter according to claim 1, further comprising initiation means for detecting the presence of a rapid ventricular rate of said patient's heart and for initiating the operation of said digitizing means.

3. A cardioverter according to claim 2 wherein said analysis means comprises means for providing a series of said width measurements based on said digital data stored during a plurality of said time windows.

4. A cardioverter according to claim 3 wherein said ventricular tachycardia detection means comprises means for determining whether more than a predetermined number of the width measurements within said series of width measurements exceed a predetermined width criterion.

5. A cardioverter according to claim 4, further comprising interval measuring means for measuring R—R intervals between successive ones of said R-wave signals and control means responsive to said interval measuring means for permitting operation of said analysis means only following a said R-wave signal which follows an immediately preceding R-wave signal by a said R—R interval which meets predetermined duration criteria.

6. A method of cardioversion, comprising:
   sensing electrical signals from a ventricle of a patient's heart;
   detecting the occurrence of a depolarization of the ventricle of said patient's heart;
   converting said electrical signals from the ventricle of said patient's heart to digital signals indicative of a magnitude of said electrical signals and storing said digital signals sequentially;
   defining a time window extending from a point in time prior to said detected depolarization until a point in time following said detected depolarization; and
   analyzing the said digital signals stored in the said time window, said analyzing step in turn comprising:
      sequentially scanning through the said digital signals stored during a said time window in a first direction and measuring the difference between individual ones of said stored digital signals and others of said stored digital signals to determine whether said measured differences exceed a predetermined threshold;
      counting the number of sequential ones of said difference measurements exceeding said predetermined threshold and defining an endpoint each time said number of said difference measurements exceeding said predetermined threshold reaches a predetermined count;
      measuring a time interval between a the first said endpoint to occur during said scanning and a last said endpoint to occur during said scanning to provide an R-wave width measurement; and
      detecting the occurrence of a ventricular tachycardia and triggering delivery of said therapy if said width measurement meets predetermined criteria.

7. A method according to claim 6, further comprising the step of detecting the presence of a rapid ventricular rate of said patient'heart and in response initiating said converting step.

8. A method according to claim 7 wherein said analyzing step comprises providing a series of said width measurements based on said digital data stored during a plurality of said time windows.

9. A method according to claim 8, wherein step of detecting the occurrence of ventricular tachycardia comprises determining whether more than a predetermined number of the said width measurements within said series of width measurements exceed a predetermined width criterion.

10. A method according to claim 9, further comprising step of measuring the durations of R—R intervals between successive ones of said detected depolarizations and performing said analyzing step only following a said detected depolarization which follows an immediately said detected depolarization by a said R—R interval which meets predetermined duration criteria.

* * * * *

UNITED STATES PATENT AND TRADEMARK OFFICE
CERTIFICATE OF CORRECTION

PATENT NO. : 5,312,441
DATED : May 17, 1994
INVENTOR(S) : Steven J. Mader, et al It is certified that error appears in the above-indentified patent and that said Letters Patent is hereby corrected as shown below:

Column 12, Lines 40-41, after "parameter equal to", please insert -- one. However, as illustrated in Figure 7, a book back--.

Column 13, Line 16, delete "FIG. 3,", and insert in its place --Figure 6,--.

Column 13, Line 28, delete "PRT", and insert in its place --PTR--.

Column 13, Line 32, delete "PRT", and insert in its place --PTR--.

Column 13, Line 42, delete "PRT", and insert in its place --PTR--.

Signed and Sealed this

Eighteenth Day of October, 1994

*Attest:*

BRUCE LEHMAN

*Attesting Officer*   *Commissioner of Patents and Trademarks*